United States Patent [19]

Cort

[11] 4,261,980
[45] Apr. 14, 1981

[54] METHOD FOR PROPHYLAXIS AND/OR TREATMENT OF SICKLE CELL DISEASE

[75] Inventor: Joseph H. Cort, New York, N.Y.

[73] Assignee: Vega Laboratories, Inc., Tucson, Ariz.

[21] Appl. No.: 150,700

[22] Filed: May 16, 1980

[51] Int. Cl.³ ............................................. A61K 37/00
[52] U.S. Cl. ................................................... 424/177
[58] Field of Search ......................................... 424/177

[56] References Cited

PUBLICATIONS

*Development of Therapeutic Agents for Sickle Cell Disease*, INSERM Symposium No. 9, Rosa et al., 1979 Elsevier, North-Holland Biomed. Press, pp. 129-137.

*Primary Examiner*—Frederick E. Waddell
*Attorney, Agent, or Firm*—Kenyon & Kenyon

[57] ABSTRACT

Polypeptides which are useful in the prophylaxis and treatment of sickle cell disease are represented by the formula:

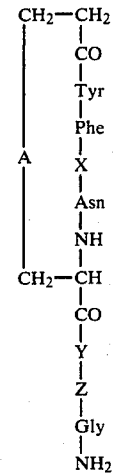

wherein X is Val or Gln; Y is Pro or dehydroPro; Z is a residue of a basic amino acid with a side chain in the D-configuration; and A is a disulfide or monocarba radical, with the proviso that when X is Gln, Y is Pro and Z is D-Arg, then A is mono-carba.

11 Claims, No Drawings

METHOD FOR PROPHYLAXIS AND/OR TREATMENT OF SICKLE CELL DISEASE

The present invention is concerned with a method for the prophylaxis and/or treatment of sickle cell disease.

BACKGROUND

Sickle cell disease, particularly in its homozygous form, is the result of a hereditary defect in hemoglobin biosynthesis which affects large numbers of the black population of the world and other located about the Mediterranean area. The hereditary molecular defect involves a single substitution of one valine residue for one glutamine residue in the beta chain of the hemoglobin molecule. This chemical substitution of a hydrophobic amino acid residue for a hydrophilic one makes the whole hemoglobin molecule slightly less water-soluble so that there is a tendency to crystallization of the molecule under two conditions: (1) when the pH of the extracellular body fluids decreases (i.e. acidosis with or without a high $pCO_2$), or (2) when the concentration of water in these fluids decreases (i.e. dehydration). This it is found that sickle cell "crises" often start at night when there is a natural tendency to dehydration and metabolic acidosis during sleep (no oral hydration, continued formation of urine, tendency to hypoventilation, etc.).

Crystallization of the hemoglobin in the red blood cells distorts their shape into sickle-like cells, and the latter tend to have difficulty in passage through capillaries. A large concentration of sickled cells in the circulation causes aggregation of the cells in capillaries, decreases capillary flow and oxygenation of tissues, increases peripheral vascular resistance and puts a load on the heart which may result in congestive heart failure. Cases vary in frequency and severity of such "crises", the frequency varying from weekly to monthly. Severe cases have short lives, with a particularly high mortality in young patients in many parts of the African continent. Pharmaceutical preparations so far used in an attempt to alter this sickling response of the red blood cells have in practically all instances proved as toxic or more toxic than the disease itself.

It has been known for some time that if the concentration of water surrounding sickled cells is increased either in vivo or in vitro, the sickling phenomenon can be reversed. Unfortunately, even with very large intravenous infusions of hypotonic fluids a state of sufficient hypo-osmolality is practically impossible to induce in patients, since their kidneys get rid of the water load as fast as it is given.

DESCRIPTION OF THE INVENTION

In accordance with this invention, sickle cell disease is treated by administering to a human patient an effective amount of synthetic polypeptide analog of vasopressin represented by the general formula:

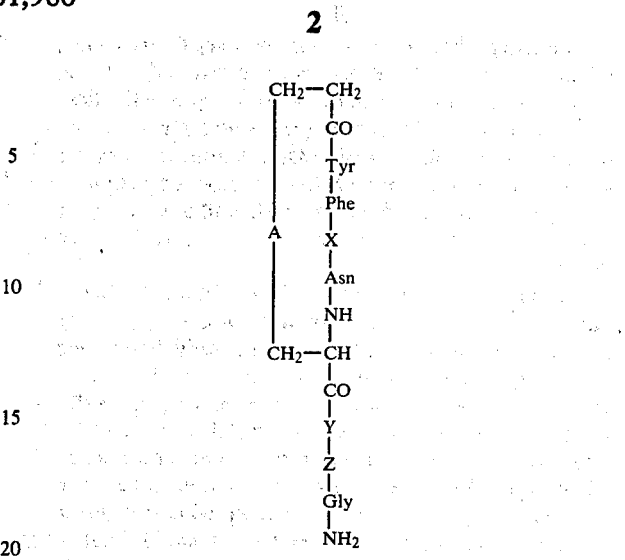

wherein X is Val or Gln; Y is Pro of dehydroPro; Z is a residue of an alpha-amino acid having a basic aliphatic side chain in the D-configuration containing from 2 to 5 carbon atoms and having on the terminal carbon a basic group such as the amino or quanidino group, such as arginine, lysine and ornithine; and A is a disulfide (—S—S—) or monocarba (—S—$CH_2$— or —$CH_2$—S—) radical; with the proviso that when X is Gln, Y is Pro and Z is D-arginine, than A is monocarba. By the term "residue" of an amino acid is meant the divalent radical formed by removal of the hydrogen atom from the alpha-amino group and the removal of the hydroxyl group from the carboxyl group of the amino acid. According to accepted conventions, Tyr represents the residue of tyrosine, Phe represents the residue of phenylalanine, Gln represents the residue of glutamine, Asn represents the residue of asparagine, Val represents the residue of valine, Pro represents the residue of proline and Gly represents the residue of glycine.

Polypeptides within the scope of the general formula (I) are disclosed in U.S. Pat. No. 3,980,631. These, as well as still other polypeptides within the scope of the formula, may be synthesized from individual amino acids or amino acid precursors by procedures described in U.S. Pat. No. 3,980,631. A currently preferred polypeptide within the above-defined class of vasopressin analogs is 1-deamino-6-carba-8-D-arginine vasopressin, also known as 6-monocarba desmopressin or dCDAVP. The preparation of this polypeptide is described in Example 2 of U.S. Pat. No. 3,980,631. These polypeptides are known to be pharmaceutically useful as antidiuretics.

Particularly preferred polypeptide analogs fall into three categories: (1) Those where X is the residue of valine (Val); (2) those where Y is the residue of dehydroproline (dehydroPro); and (3) those where A is monocarba. Polypeptides wherein A is monocarba are much longer acting than those where A is disulfide, and have an antidiuretic action which is more than three times that of the corresponding analog wherein A is disulfide. Those analogs wherein X is Val and Y is dehydroPro have higher peak antidiuretic potencies, and thus can be employed at lower dosages than other polypeptides.

In accordance with with invention, the above-identified polypeptides are safe and effective agents, when used in combination with low salt, high water intake, for inducing a hypoosmotic state in body fluids which, when used prophylactically, prevent red cell sickling, or when used to treat a sickling crisis, reverse sickling.

These polypeptides are uniquely suited for use in the treatment or prophylaxis of sickle cell disease. They are active anti-diuretics, which have prolonged action of from 7 to 72 hours, and which are devoid of vascular or non-vascular smooth muscle side effects at effective dosages.

The amount of polypeptide which is employed is not narrowly critical, and it is highly variable depending upon the patient. The amount can be readily determined on a case-by-case basis in accordance with known procedures to ascertain the amount of polypeptide sufficient to induce a state of hypo-osmolality sufficient to inhibit or reduce red cell sickling. As a general rule, an adequate level of hypo-osmolality is a level which is at most about 10 percent below the accepted normal value for serum osmolality (i.e., about 300 m Osm/l). That is, serum osmolality should be from about 270 to about 300 m Osm/l, and preferably from about 270 to about 275 m Osm/l. In addition, the serum sodium concentration is generally in the range of from about 120 to about 130 mM, as contrasted with a normal serum sodium concentration of about 140 mM.

The polypeptide may be administered to the patient in any convenient manner. Thus, it can be administered by injection. Alternatively, and preferably, especially where the polypeptide is to be used by the patient, it is administered intranasally, i.e., in the form of nose drops. In the latter case, however, the applied dosage of polypeptide per individual should be about ten times the dosage given by injection to achieve a comparable effect. A typical regimen for intranasal administration of polypeptide comprises administration of about 0.1 ml of a 100 μg/ml solution of polypeptide every 6 to 12 hours.

The polypeptide is administered in solution in a suitable solvent, preferably water. The solution may contain various additives generally known to the art. A preferred medium is physiological saline solution. When the polypeptide is one where A is disulfide, the solution is preferably acidic, having a pH of from about 3 to about 5, and especially about 4, to stabilize the polypeptide; otherwise, a solution having about neutral pH is satisfactory. it is also desirable to include small amounts of bacteriostat, e.g., chlorobutanol, to minimize bacterial contamination in the intranasal preparation.

The concentration of polypeptide in the solution is not narrowly critical, and can range from about 1 μg/ml to 1000 μg/ml or higher, depending upon the intended mode of administration and dosage. In general, solutions intended for intranasal applications will contain higher concentrations of polypeptide than solutions intended to be administered by injection. Thus, solutions for intranasal administration ordinarily will contain from about 100 to about 400 μg polypeptide per milliliter, whereas injectable solutions will contain of the order of about 4 to about 10 μg polypeptide per milliliter.

What is claimed is:

1. A method for the prophylaxis or treatment of sickle cell disease which comprises administering to a human patient an effective amount of a polypeptide represented by the formula:

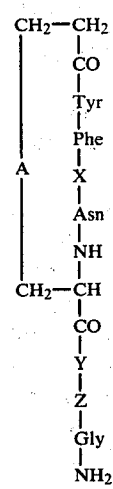

wherein X is Val or Gln; Y is Pro or dehydroPro; Z is a residue of an alpha-amino acid having a basic side chain in the D-configuration containing from 2 to 5 carbon atoms and having on the terminal carbon a basic group; and A is a disulfide (—S—S—) or monocarba (—S—CH$_2$—) radical; with the provisio that when X is Gln, Y is Pro and Z is D-arginine, then A is monocarba.

2. A method according to claim 1 wherein X is Val.

3. A method according to claim 1 wherein Y is dehydroPro.

4. A method according to claim 1 wherein A is monocarba.

5. A method according to claim 1 wherein X is Val; Y is dehydroPro and A is monocarba.

6. A method according to claim 1 wherein said polypeptide is 1-deamino-6-carba-8-D-arginine vasopressin.

7. A method according to claim 1 comprising administering said polypeptide to a patient undergoing a sickling crisis.

8. A method according to claim 1 comprising administering said polypeptide prophylactically to said patient.

9. A method according to claim 1 wherein said polypeptide is administered intranasally.

10. A method according to claim 1 wherein said polypeptide is administered in an amount sufficient to reduce serum osmolality to from about 270 to about 275 m Osm/l.

11. A method according to claim 1 wherein said polypeptide is administered in an amount sufficient to achieve a serum sodium concentration in the range of from about 120 to about 130 mM.

* * * * *